United States Patent
Tamersoy et al.

(10) Patent No.: US 10,478,149 B2
(45) Date of Patent: Nov. 19, 2019

(54) METHOD OF AUTOMATICALLY POSITIONING AN X-RAY SOURCE OF AN X-RAY SYSTEM AND AN X-RAY SYSTEM

(71) Applicant: Siemens Healthcare GmbH, Erlangen (DE)

(72) Inventors: Birgi Tamersoy, Erlangen (DE); Vivek Kumar Singh, Princeton, NJ (US); Yao-jen Chang, Princeton, NJ (US); Susanne Dornberger, Erlangen (DE); Ralf Nanke, Neunkirchen am Brand (DE); Terrence Chen, Princeton, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 510 days.

(21) Appl. No.: 15/437,797

(22) Filed: Feb. 21, 2017

(65) Prior Publication Data

US 2018/0235566 A1    Aug. 23, 2018

(51) Int. Cl.
*A61B 6/00* (2006.01)

(52) U.S. Cl.
CPC ............ *A61B 6/587* (2013.01); *A61B 6/4417* (2013.01); *A61B 6/4458* (2013.01); *A61B 6/4464* (2013.01)

(58) Field of Classification Search
CPC ....................................................... A61B 6/587
See application file for complete search history.

(56) References Cited

U.S. PATENT DOCUMENTS

| 8,696,200 B2 | 4/2014 | Mohr |
| 9,273,956 B2 | 3/2016 | Egli et al. |
| 2003/0194056 A1* | 10/2003 | Spahn .................... A61B 6/08 |
| | | 378/205 |

FOREIGN PATENT DOCUMENTS

| DE | 102011083634 A1 | 3/2013 |
| DE | 102015211057 A1 | 12/2016 |
| WO | 0187136 A2 | 11/2001 |
| WO | 2010132002 A1 | 11/2010 |

OTHER PUBLICATIONS

Extended Search Report dated Jul. 8, 2018 in EP Application No. 18157301.5, 9 pages.
G. Schweighofer and A. Pinz, "Robust Pose Estimation from a Planar Target," Graz University of Technology—Technical Report, TR-EMT-2005-01 (May 13, 2005).

* cited by examiner

*Primary Examiner* — Dani Fox

(57) ABSTRACT

A method and a system for automatically aligning a positionable X-ray source of an X-ray system in alignment with a mobile X-ray detector is disclosed where the X-ray system detects the position of the mobile X-ray detector using a 3D camera and then driving the positionable X-ray source to a position in alignment with the mobile X-ray detector.

20 Claims, 7 Drawing Sheets

Input
110
220
210

Point & Radial Marker Detection

Correspondence Matching

Corner & Handle Pattern Detection

METHOD OF AUTOMATICALLY POSITIONING AN X-RAY SOURCE OF AN X-RAY SYSTEM AND AN X-RAY SYSTEM

CROSS-REFERENCE TO RELATED APPLICATIONS

None.

FIELD

The invention relates to a method for automatically positioning an X-ray source of an X-ray system and an X-ray system for carrying out such a method.

BACKGROUND

X-ray systems where both the X-ray source and the X-ray detector have several degrees-of-freedom (DOF) provide a significant advantage in terms of patient positioning flexibility. Such systems utilize mobile X-ray detectors, which can be positioned anywhere in the patient space and results in more robust X-ray systems. Such systems enable high quality X-ray examinations to be carried out for more specific regions of interests and for a wider range of patients (e.g. in cases of serious trauma). The mobile X-ray detectors can be connected by wires or be wireless.

However, this flexibility comes at a price. In order to acquire high quality X-ray images, the X-ray source, the region-of-interest on the patient, and the X-ray detector should be well aligned. The better the alignment, the higher the quality of the X-ray image will be. With mobile X-ray detectors, this alignment is performed in two steps: aligning the X-ray detector with respect to the region-of-interest, and then aligning the X-ray source with respect to the X-ray detector. Conventionally, an operator performs this alignment manually by positioning the mobile X-ray detector at a location so that an X-ray image of a region of interest on the patient can be recorded. Then, the operator manually aligns and positions the X-ray source relative to the X-ray detector. Because the alignment is performed manually, the quality of the alignment is not consistent and difficult to reproduce every time.

Thus, there is a need for improving the method of aligning the X-ray source to the X-ray detector.

SUMMARY

According to various embodiments, a method can be provided that ensures simple and quick positioning of the positionable X-ray source. According to further embodiments, a suitable X-ray system for carrying out the method can be provided.

According to various embodiments, a method for determining the position of a mobile X-ray detector in an X-ray system, wherein the X-ray system is provided with a 3D camera is disclosed. The method comprises:
acquiring an image of the mobile X-ray detector using the 3D camera, wherein the mobile X-ray detector has a X-ray receiving portion on a planar surface and a plurality of passive markers provided on the planar surface having the X-ray receiving portion;
detecting the plurality of passive markers and the markers' pattern, wherein the pattern of the markers' defines the plane of the mobile X-ray detector having the X-ray receiving portion;
estimating the plane of the mobile X-ray detector's X-ray receiving portion;
estimating 6 DOF pose of the mobile X-ray detector, wherein the 6 DOF pose defines the position of the mobile X-ray detector in the 3D camera's coordinate system; and
transforming the position of the mobile X-ray detector in the 3D camera's coordinate system into a position in the X-ray base coordinate system.

According to some embodiments, a method for automatically aligning a positionable X-ray source of an X-ray system in alignment with a mobile X-ray detector, wherein the X-ray system is equipped with a 3D camera is disclosed. The method comprises:
manually positioning the mobile X-ray detector, wherein the mobile X-ray detector has a X-ray receiving portion on a planar surface and a plurality of passive markers provided on the planar surface having the X-ray receiving portion;
positioning the 3D camera so that the mobile X-ray detector is within the field of view of the 3D camera;
automatically determining the position of the mobile X-ray detector using the 3D camera, wherein automatically determining the position of the mobile X-ray detector comprises:
acquiring an image of the mobile X-ray detector using the 3D camera;
detecting the plurality of passive markers and the markers' pattern in the acquired image, wherein the pattern of the markers' defines a plane of the mobile X-ray detector having the X-ray receiving portion;
estimating the plane of the mobile X-ray detector's X-ray receiving portion;
estimating 6 DOF pose of the mobile X-ray detector, wherein the 6 DOF pose defines the position of the mobile X-ray detector in the 3D camera's coordinate system; and
transforming the position of the mobile X-ray detector in the 3D camera's coordinate system into a position in the X-ray base coordinate system which defines an aligned position; and
automatically positioning the X-ray source to the aligned position by driving the X-ray tube robot system which brings the X-ray source in alignment with the mobile X-ray detector.

BRIEF DESCRIPTION OF THE DRAWINGS

All drawing figures are schematic and are not necessarily to scale.

FIG. 2 is a detailed view of the mobile X-ray detector in FIG. 1.

DETAILED DESCRIPTION

This description of the exemplary embodiments is intended to be read in connection with the accompanying drawings, which are to be considered part of the entire written description.

Figure 1A:
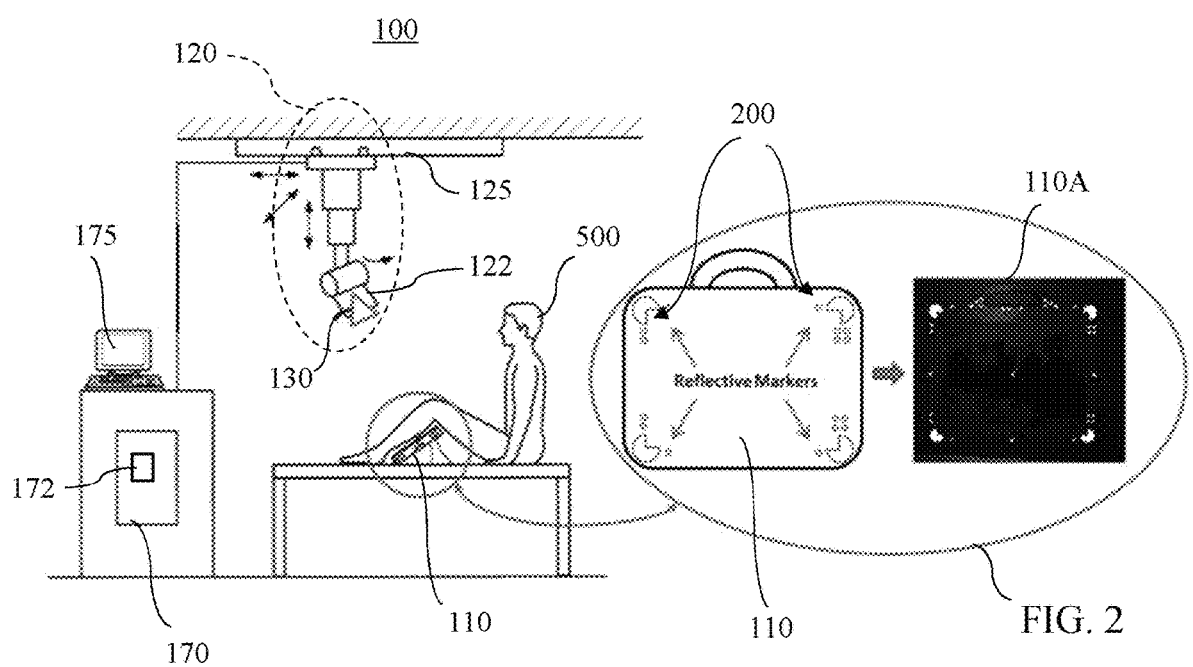
FIG. 1A shows a view of an X-ray system utilizing a mobile X-ray detector according to various embodiments.

We present an X-ray system and a method for automatic alignment of the X-ray source and the mobile X-ray detector that utilizes two features: 1) a 3D camera configured and adapted with an optical depth sensing and an imaging capabilities provided on a positionable X-ray source, and 2) a mobile X-ray detector having passive markers placed thereon. One embodiment of such X-ray system 100 is illustrated in FIG. 1A. The X-ray system 100 comprises an X-ray tube robot system 120, a positionable X-ray source 122, an X-ray source base 125, a 3D camera 130 mounted on the X-ray source, a mobile X-ray detector 110, and a system controller 170. The 3D camera can be attached to an appropriate location on the X-ray source depending on the physical configuration of the particular X-ray source 122. In some embodiments, the 3D camera can be attached to a rear side of the X-ray source.

In some embodiments, the mobile X-ray detector 110 advantageously is formed by a mobile flat-panel detector for recording high-quality X-ray images. In some embodiments, the mobile X-ray detector 110 is wireless and is configured with transmission and reception means for wireless communication with the system controller 170, for example, for transmitting the acquired X-ray images.

In some embodiments, the mobile X-ray detector has a wired connection to the X-ray system and so quick and error-free communication between the X-ray detector and a component of the X-ray system differing therefrom is ensured.

The system controller 170 is provided for effectuating the overall operation of the X-ray system 100. For example, the system controller 170 is configured with appropriate hardware and software necessary to control the operation of all of the components of the X-ray system 100 including controlling and interfacing with the 3D camera 130, interfacing, controlling and driving the positionable X-ray source 122, acquiring RGB/IR images using the 3D camera, processing of the RGB/IR image data and depth sensor data received from the 3D camera and determining the position of the mobile X-ray detector 110, calculating the alignment position of the X-ray source, driving the X-ray image acquisition function of the X-ray system 100.

The system controller 170 can further have a network interface 172 for communicating with other devices in the system via a network. For example, the network interface 172 is configured to carry out data transfer with the mobile X-ray detector 110. Additionally, the X-ray system generally has an image processing system for processing X-ray images, a user interfacing unit 175 comprising a touch/display screen, a keyboard, a mouse, etc. for the X-ray technician to interface with the X-ray system. Provision can also be made for the mobile X-ray detector 110 to have a wired connection to the system controller 170 for data transfer. The X-ray detector 110 can be manually positioned anywhere about the patient 500 by an X-ray technician in order to record X-ray images of a region of interest on the patient. In this example illustration, the mobile X-ray detector 110 is positioned for an X-ray examination of a patient 500's femur region.

The X-ray tube robot system 120 is configured and adapted to be driven by the system controller 170 for articulating the positionable X-ray source into any desired position to align the X-ray source 122 with the mobile X-ray detector 110. For example, the X-ray tube robot system 120 can comprise a robotic arm on which the X-ray source is arranged. Such a robotic arm allows a particularly variable adjustability of the X-ray source. Alternatively, the X-ray tube robot system 120 can comprise a telescoping arm that is hung from overhead tracks.

According to an aspect of the present disclosure, the optical depth sensing feature of the 3D camera 130 allows the camera to determine the distance between the camera and the surfaces seen in its image field. In other words, the 3D camera produces a digital image of its image field and also produces the distance associated with each pixel in the image (also referred to as the depth). The 3D camera can be configured to perform the optical depth sensing by an IR-based depth sensing that acquires images in the infra-red spectrum as well as the depth values for every pixel in its field of view. Alternatively, the 3D camera can be configured to perform the depth sensing using visible light spectrum. In either case, a plurality of passive markers 200 are placed at designated points on the surface of the mobile X-ray detector 110 that would allow the 3D camera to see and resolve the orientation of the mobile X-ray detector 110 and to determine the distance between the X-ray source 122 and the mobile X-ray detector 110. The plurality of passive markers 200 are provided in shapes and patterns that can uniquely identify each of the corners of the mobile X-ray detector 110. By detecting the plurality of passive markers 200 in the digital image provided by the 3D camera, the system controller 170 uses this information to calculate the accurate position and orientation of the mobile X-ray detector 100 in the X-ray system and then automatically aligns the positionable X-ray source 122 to the mobile X-ray detector 110. The system controller 170 accomplishes this by performing transformations between the coordinate system of the 3D camera, the coordinate system of the X-ray base, and the coordinate system of the positionable X-ray source. The result is more accurate and repeatable alignment of the X-ray source and the mobile X-ray detector compared to the conventional manual alignment.

In the embodiments where the 3D camera is an infrared (IR)-based camera and depth sensor, the passive markers 200 are IR reflective markers that have strong response on the infra-red light projected onto the markers and allows the 3D camera to see the IR reflective markers and determine the distance to the mobile X-ray detector and the detector's orientation. The benefit of using the IR reflective markers is that the color of the markers can be made to blend in with the color of the detector such that the markers are not so noticeable in the visible spectrum. The IR-based 3D camera produces an IR digital image in which each pixel has an IR value and a depth (or distance) value. The digital image data obtained from such IR-based 3D camera will be referred to herein as an IRD image.

In the embodiments where the 3D camera is a visible light spectrum based camera and depth sensor, the passive markers 200 have a color that is visually distinguishable from the color of the mobile X-ray detector's surface, so that the 3D camera can see the passive markers in visible light spectrum and determine the distance to the mobile X-ray detector and the detector's orientation. Such visible light 3D camera produces an RGB (Red, Green, Blue) digital image. The digital image data obtained from such 3D camera is typically referred to as an RGBD (RGB+Depth) image, which includes an RGB image, in which each pixel has an RGB value, and a depth (or distance) value.

The position of the mobile X-ray detector is calculated from the distance and orientation information gathered from the passive markers 200 using the 3D camera and represented as a 6 DOF (degrees of freedom) pose information on the mobile X-ray detector.

The associated X-ray examination workflow is as follows: position the patient appropriately; position the mobile X-ray detector with respect to the region-of-interest; acquire a pair of images of the scene (one IR and one depth) using the 3D camera; compute the 6 DOF pose of the X-ray detector using the pair of images; automatically position the X-ray source to the aligned position that is in alignment with the mobile X-ray detector based on the 6 DOF pose information on the mobile X-ray detector; then record one or more X-ray images of the region-of-interest.

According to the present disclosure, the system controller 170 is configured to perform the portions of the above-mentioned workflow after the mobile X-ray detector is positioned in place with respect to the region-of-interest. In preferred embodiments, the system controller 170 is configured to initiate the process when a single command is inputted via the system controller's operator input device 175. For example, the single command can be a voice command, a click of a key, a click of a mouse, a touch on a touch screen, etc. The rest of the workflow does not require any manual intervention from the X-ray technician and the resulting alignment between the X-ray detector and the X-ray source is much more accurate than the conventionally achieved alignment.

In order to use the 3D camera to generate the 6 DOF pose information on the mobile X-ray detector that is reliable and accurate, the 3D camera needs to be calibrated.

System Calibration

The calibration of the 3D camera involves: (1) the intrinsic calibration of the 3D camera itself, and (2) the transformations between the 3D camera coordinate system and the X-ray base coordinate system. The transformations between the 3D camera coordinate system and the X-ray base coordinate system is necessary because the 3D camera 130 and the X-ray source 122 are mounted on the X-ray base 125 where the X-ray source 122 and the 3D camera 130 are movable relative to the X-ray base 125. The alignment of the X-ray source 122 to the X-ray detector 110 involves transformations between the three coordinate systems: the X-ray base coordinate system; the X-ray source coordinate system; and the 3D camera coordinate system. The X-ray base coordinate system is defined with a point on the X-ray base 125 as the reference origin. The X-ray source coordinate system is defined with a point on the positionable X-ray source 122 as the reference origin. The 3D camera coordinate system is defined with a point on the 3D camera as the reference origin. Thus, in order for the X-ray system to operate properly, the transformations between the three coordinate systems have to be calibrated. Because the mobile X-ray detector 110 is detected by optically sensing the passive markers 200 using the 3D camera 130, the mobile X-ray detector 110 is detected in the 3D camera coordinate system.

The intrinsic calibration of the 3D camera provides a metric conversion for each pixel of the acquired image to the physical metric dimension in the 3D camera's coordinate system. The standard approach for camera intrinsic calibration is achieved by placing a planar calibration target with known patterns (chessboard or dot-pattern grid) in front of the camera at various relative poses with respect to the camera. The intrinsic calibration of the camera provides information on the intrinsic properties of the camera including its focal length, principal point, and radial distortion parameters. More formally, the goal of the intrinsic calibration is to obtain the intrinsic properties of the camera via a set of known 3D points $\{P^j\}$ on the calibration target and its 2D correspondences $\{p_i^j\}$ on the i-th image. This is achieved by minimizing the re-projection error between the 2D projections and corresponding measured points. That is, $$K_c, \{R_i\}, \{t_i\} = \mathrm{argmin}_{K_c, \{R_i\}, \{t_i\}} \Sigma_i \Sigma_j \| p_i^j - f(R_i P^j + t_i, K_c, d_c) \|^2, \quad (1)$$

where f(.) is the 3D to 2D projection function from camera's coordinate system to its image plane, $K_c$ is the intrinsic calibration matrix containing the focal length and skew of the 3D camera's two axes and the principal point on the image, and $d_c$ is its lens distortion vector. $R_i$ and $t_i$ are the extrinsic parameters describing the pose of the camera in the i-th image. The optimization is carried out by using conventional calibration algorithms, e.g. Zhang 2000, Bouguet MCT, etc.

Depending on the imaging system used by the 3D camera, the pattern needs to be clearly detectable by the camera. For a 3D camera based on the normal RGB imaging system, placing dark patterns on top of a white surface is a common choice. For IR-based 3D camera, IR reflective patterns will be needed. The quality of the intrinsic calibration of the camera affects the final alignment accuracy. As with any calibration setup, having more images with large target variability improves the calibration quality, but at the same time makes the corresponding acquisition process quite cumbersome. In order to overcome this, we introduce a dual-modal IR/RGB calibration target 400, see FIGS. 3 and 4, and accompany this target with an automatic data acquisition protocol.

Figure 3:
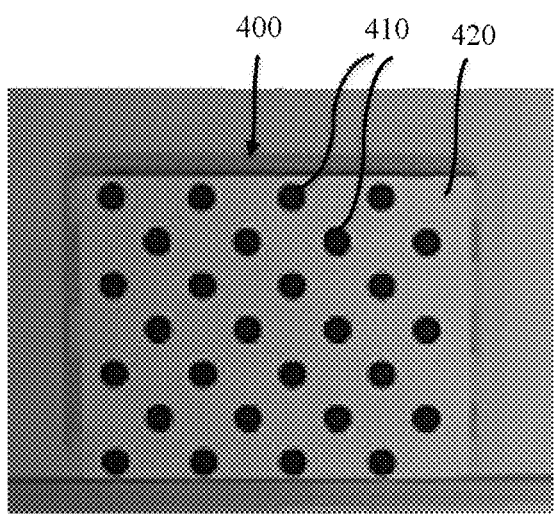
FIG. 3 shows a dual-modal target according to the present disclosure viewed in the RGB imaging mode.
Figure 4:
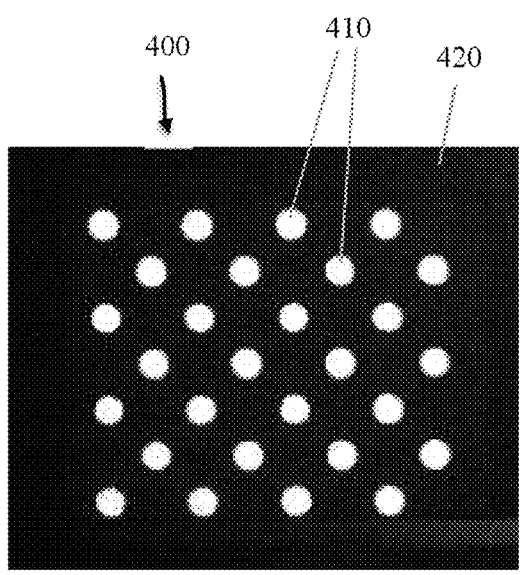
FIG. 4 shows a dual-modal target according to the present disclosure viewed in the IR imaging mode.

Our dual-modal IR/RGB calibration target 400 consists of reflective markers 410 placed in a dot-pattern as illustrated in FIGS. 3 and 4. FIG. 3 shows the dual-modal target 400 viewed in the RGB imaging mode. The dark color of the reflective markers 410 arranged in a dot-pattern contrasted against the light background 420 provides a high-contrast RGB image. FIG. 4 shows the dual-modal target 400 viewed in the IR imaging mode. The reflective markers 410 appear white because these reflective markers reflect IR from the IR source back to the IR camera and the background 420 appears dark because the light background surface diffuses and/or absorbs IR. Using the dual-modal target we can simultaneously acquire very high-contrast images from both the RGB mode and the IR mode of the dual-mode 3D camera, and automatically establish point correspondences between the acquired images.

We then utilize the positionable X-ray source for automatically acquiring a very large set of calibration image pairs under various X-ray source poses and positions. Furthermore, since the dual-modal target is easily detectable in both modalities, we can ensure a large variability among the captured image pairs as we capture them while keeping the calibration target inside the 3D camera's field of view.

Once the intrinsic calibration of the imaging system of the 3D camera is completed, the kinematic calibration is performed to establish the transformation between the X-ray base coordinate system and 3D camera coordinate system. The calibration of the transformation between the X-ray base coordinate system and the X-ray source coordinate system follows the kinematic mechanism of the whole X-ray tube robot system 120. This can either be derived from the manufacturer's specification for the X-ray tube robot system 120 or utilize the kinematic calibration to establish a transformation between the coordinate system of the 3D camera and the coordinate system of the X-ray source coordinate system. Such kinematic calibration is described in the U.S. patent application Ser. No. 14/881,526 filed on Oct. 13, 2015, the disclosure of which is incorporated herein by reference in its entirety. Once the kinematic calibration is completed, the 3D camera is ready for use.

Computing the 6 DOF Pose of the X-Ray Detector

Figure 5:
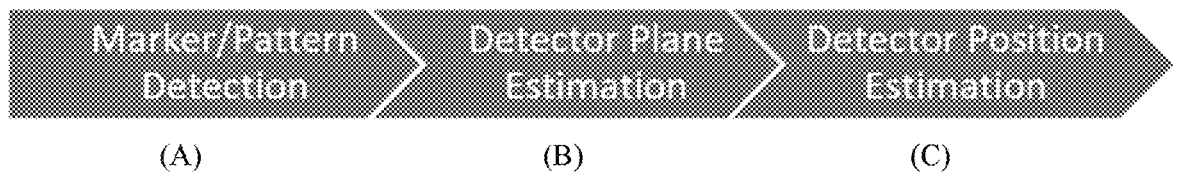
FIG. 5 shows the sequence of the three main modules involved in the automatic computation of the 6 DOF pose of the mobile X-ray detector according to the present disclosure.

According to an aspect of the present disclosure, automatic computation of the 6 DOF pose of the X-ray detector 110 will now be described. This is achieved through three process components: (A) marker/pattern detection, (B) mobile X-ray detector plane estimation, and (C) mobile X-ray detector position estimation, as depicted in FIG. 5 in sequence.

(A) Marker/Pattern Detection

For this discussion, an IR-based 3D camera embodiment is assumed. Given an input IRD image of a mobile X-ray detector 110 such as the one shown in FIG. 6A, the first step is detecting the passive reflective markers 200 in the image. In this embodiment the passive reflective markers 200 comprise the point markers 210 and the radial corner makers 220 provided in patterns to uniquely identify the specific corners of the mobile X-ray detector 110. The smaller point markers 210 are detected by convolving the input image with a simple ring-like template, whereas for the larger radial corner markers 220 we use a Hough transform-based detection approach. The Hough transform is a feature extraction technique used in image analysis, computer vision, and digital image processing. The purpose of the technique is to find imperfect instances of objects within a certain class of shapes by a voting procedure.

In some embodiments where a visible light based 3D camera is used, the passive reflective markers are visible markers and the input image of the mobile X-ray detector 110 would be an RGBD image.

Figure 6A:
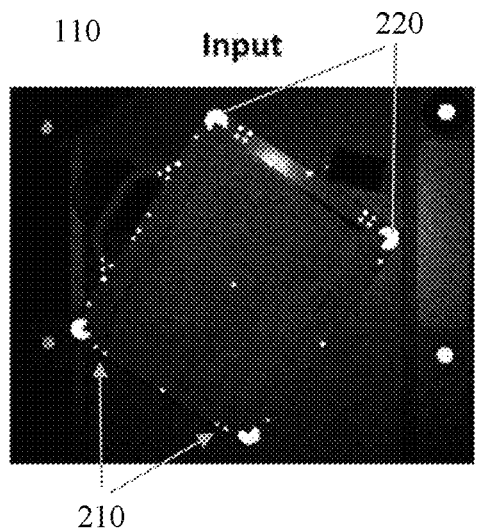
FIGS. 6A-6D show a series of IR images of a mobile X-ray detector with the passive reflective markers thereon illustrating the process of detecting the passive reflective markers on the mobile X-ray detector and matching the image to an X-ray detector template.
Figure 6B:
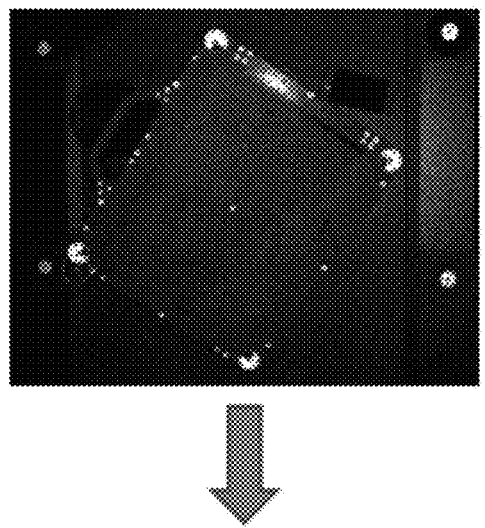

As seen in FIG. 6A, the radial corner markers are ¾ pie-shaped circles positioned at each of the detector corners oriented to allow the X-ray system to detect and recognize the four corners of the mobile X-ray detector and ascertain the relative orientation of the mobile X-ray detector. Referring to FIG. 6B, once the radial corner marker hypotheses are obtained from the marker detection phase, we then use oriented pie-shaped templates to determine the relative orientation of these markers.

Figure 6D:
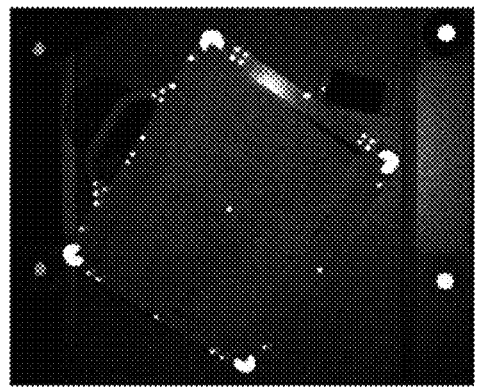
Figure 6C:
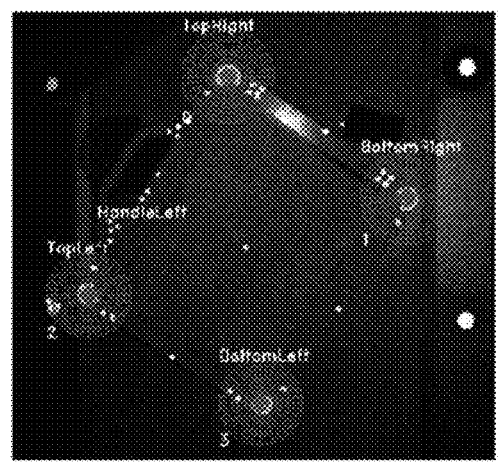

Referring to FIG. 6C, the next step in the process is determining the orientation of the mobile X-ray detector by determining the corner markers. For this, we use binning in polar coordinates where the coordinate system of each radial corner marker hypotheses is centered at the detected marker location and oriented according to the matched radial corner marker orientation. At each corner (i.e., Top Right, Bottom Right, Top Left, and Bottom Left) the combination of the radial corner marker 220 and the accompanying point markers 210 are provided in a specific pattern designating the particular corner. We use a similar strategy for detecting handle patterns. Referring to FIG. 6D, each detected and validated marker is then matched to a specific point on a pre-defined detector template. Obtaining this one-to-one correspondence is the final step of the marker/pattern detection process.

(B) X-Ray Detector Plane Estimation

Figure 7A:
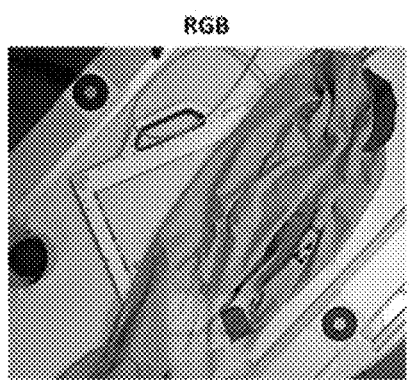
FIGS. 7A, 7B, and 7C show an RGB image, an IR image, and a point cloud representation, respectively, of a mobile X-ray detector with an occlusion between the X-ray detector and the 3D camera/X-ray source.

For a set of detected points (i.e., the reflective markers) in the IR image, the marker/pattern detection module provides one-to-one correspondences to a pre-defined detector template. In ideal conditions (i.e. no occlusion, perfect detection, etc.) this information would be enough to estimate the 6 DOF pose of the X-ray detector in the image. However, real-conditions are far from being ideal. In most X-ray examinations one, two, or three corners of the detector are occluded by the patient because the patient must be positioned between the X-ray detector and the X-ray source. For illustrative purposes, FIG. 7A shows the mobile X-ray detector whose three corners (Top Right, Bottom Right, and Bottom Left) are occluded. Furthermore, due to imaging noise and detection accuracy it is common to have a few pixel errors in marker locations. These not-so-ideal conditions make estimation of the 6 DOF pose from a very limited number of points unreliable.

Figure 7B:
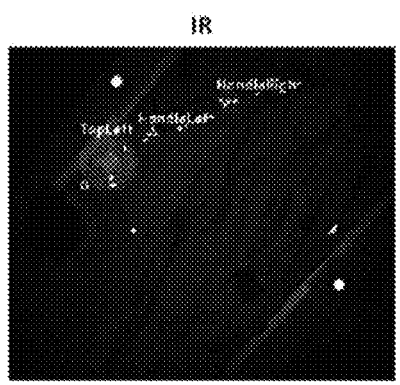
Figure 7C:
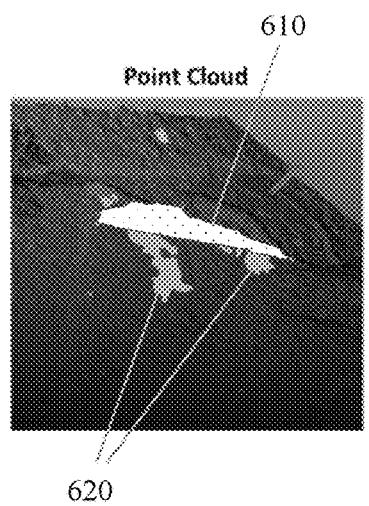

We overcome this problem by using the depth information for estimating the 3 DOF detector plane very reliably and then using this reliable plane information for estimating the 3 DOF detector position. Our detector plane estimation approach is illustrated in FIG. 7A-7C.

We first establish a region-of-interest (ROI) by using the convex hull of the detected and validated markers in the IR image. In mathematics, the convex hull or convex envelope of a set X of points in the Euclidean plane or in a Euclidean space (or, more generally, in an affine space over the reals) is the smallest convex set that contains X. Given an input set of points and assuming that the points are not on the same line, then their convex hull is a convex polygon whose vertices are some of the points in the input set of points. This ROI is depicted as the white region 610 in the point cloud of FIG. 7C. We then extend this ROI by "region growing" using the surface normal information of the neighboring points. The grown region is depicted by the gray regions 620 in the point cloud of FIG. 7C. Depending on the amount of occlusion in the image, this approach provides us with thousands of points on the detector surface, which we can then use for fitting a very reliable plane. Note that here we do not assume that all the points within the extended ROI lie on the detector surface. Our RANSAC-based robust plane fitting algorithm will be able to handle most non-detector objects (e.g. an arm or a leg) within the extended ROI since these objects would most likely be non-planar. With the reliably estimated detector plane, we know the orientation of the mobile X-ray detector 110.

(C) X-Ray Detector 6 DOF Pose Estimation

The last step in the 6 DOF pose computations is estimating the 3D position of the mobile X-ray detector 110. Given the point-correspondences to a template (marker/pattern detection module) and the reliable estimation of the mobile X-ray detector plane (X-ray detector plane estimation module), the mobile X-ray detector position estimation problem is reduced to a simple 2D-2D alignment problem. For this we use the robust pose estimation algorithm proposed by Schweighofer and Pinz, which provides another level of robustness in our 6 DOF pose computations. The 6 DOF pose for the mobile X-ray detector defines the position and the orientation of the mobile X-ray detector 110 in the 3D camera coordinate system.

Automatic Alignment of the X-Ray Source

Once the pose of the mobile X-ray detector is estimated in the form of the 6 DOF data in the 3D camera coordinate system, we can convert that location information into a location in the X-ray base coordinate system by using the transformation obtained in the system calibration step. Then the inverse kinematics described in the U.S. patent application Ser. No. 14/881,526 filed Oct. 13, 2015 can be applied to derive the optimal X-ray control parameters (by converting the location in the X-ray base coordinate system to a position in the X-ray source coordinate system) so that the positionable X-ray source 122 can be moved into an aligned position that is in alignment with the mobile X-ray detector 110.

According to some embodiments, system controller 170 takes the position information of the mobile X-ray detector 110, determines the aligned position for the X-ray source 122, aligned with the position of the mobile X-ray detector, for an X-ray, and drives the X-ray tube robot system 120 to move the positionable X-ray source 122 into the aligned position.

Figure 8:
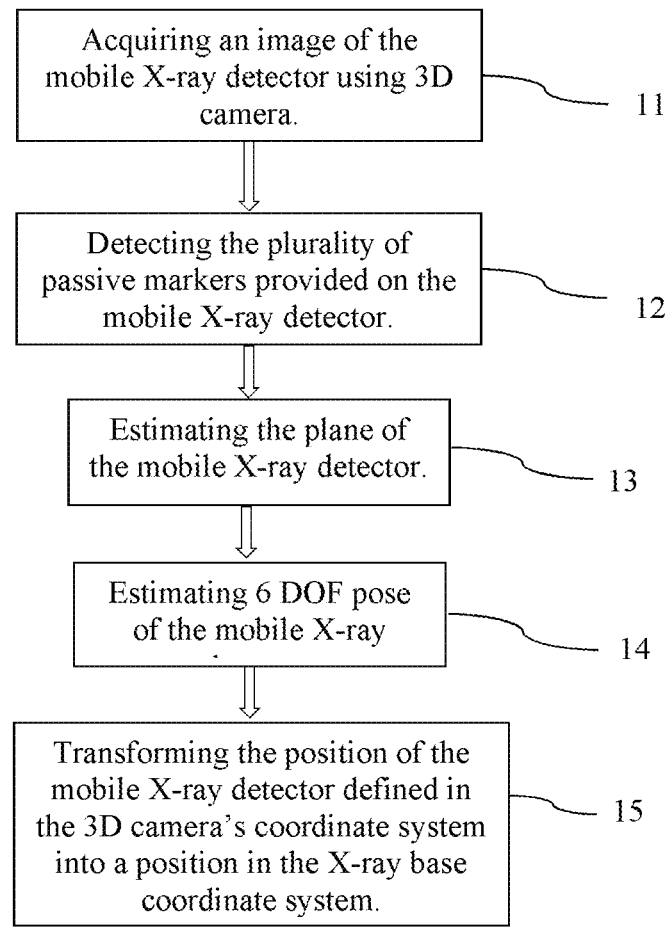
FIG. 8 shows a flowchart illustrating a method according to some embodiments.

Referring to the flowchart 10 in FIG. 8, according to some embodiments, a method is disclosed for determining the position of a mobile X-ray detector 110 in an X-ray system 100, wherein the X-ray system is equipped with a 3D camera described above. The method comprises: acquiring a digital 3D image of the mobile X-ray detector using the 3D camera (box 11), wherein the mobile X-ray detector has a X-ray receiving portion on a planar surface and a plurality of passive markers provided on the planar surface having the X-ray receiving portion; detecting the plurality of passive markers and the markers' pattern in the digital 3D image (box 12), wherein the pattern of the passive markers' defines the plane of the mobile X-ray detector having the X-ray receiving portion; estimating the plane of the mobile X-ray detector's X-ray receiving portion (box 13); estimating 6 DOF pose of the mobile X-ray detector (box 14), wherein the 6 DOF pose defines the position of the mobile X-ray detector in the 3D camera's coordinate system; and transforming the position of the mobile X-ray detector in the 3D camera's coordinate system into a position in the X-ray base coordinate system (box 15).

Figure 9:
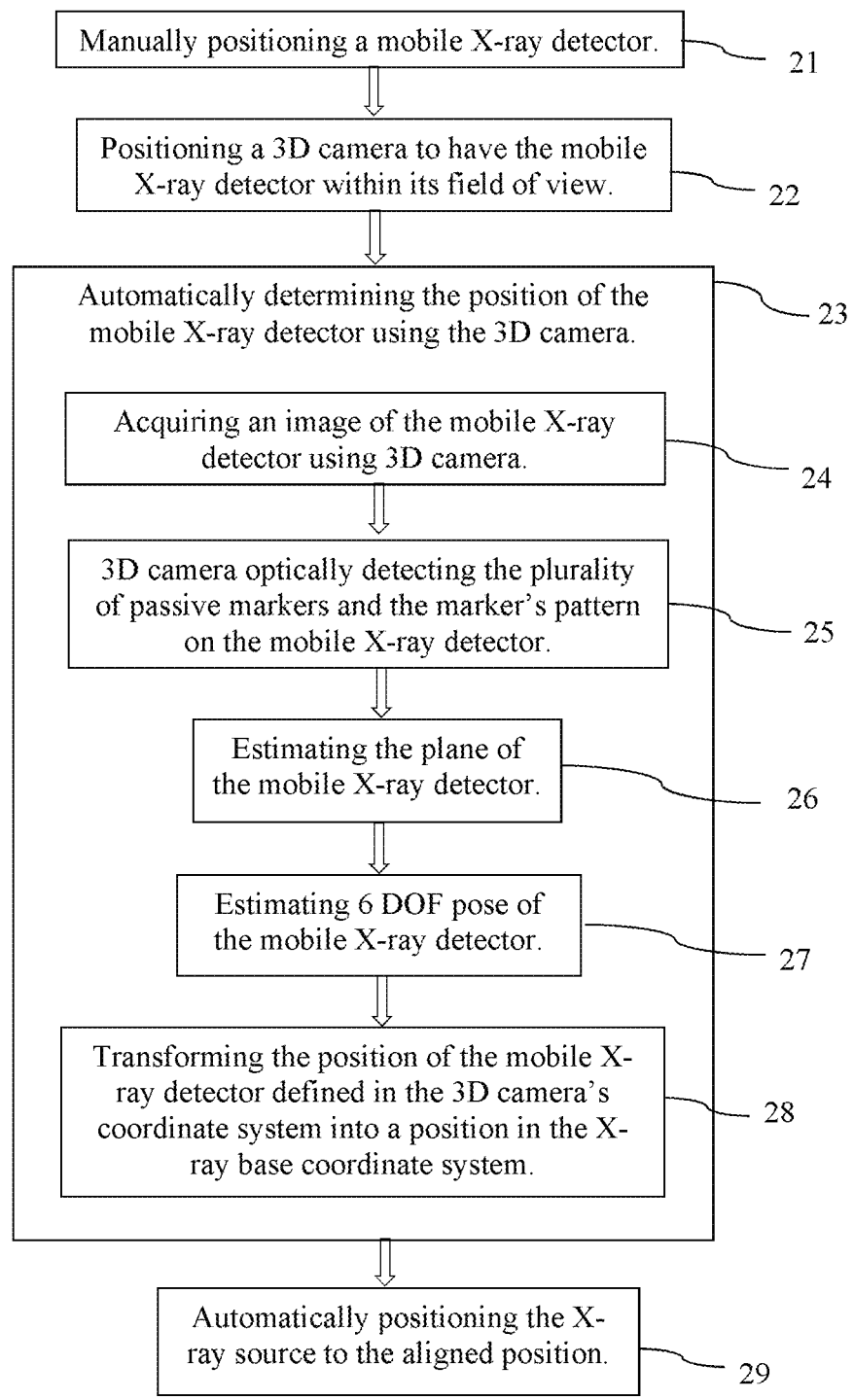
FIG. 9 shows a flowchart illustrating a method according to some other embodiments.

Referring to the flowchart 20 in FIG. 9, according to various embodiments, a method is disclosed for automatically aligning a positionable X-ray source 122 of an X-ray system 100 in alignment with a mobile X-ray detector 110, wherein the X-ray system equipped with a 3D camera described above having a field of view. The method comprises: manually positioning a mobile X-ray detector at a position to examine a region of interest on a patient (box 21), wherein the mobile X-ray detector has a X-ray receiving portion on a planar surface and a plurality of passive markers are provided on the planar surface having the X-ray receiving portion; positioning the 3D camera so that the mobile X-ray detector is within the field of view of the 3D camera (box 22); automatically determining the position of the mobile X-ray detector using the 3D camera (box 23), wherein automatically determining the position of the mobile X-ray detector comprises: acquiring a digital 3D image of the mobile X-ray detector using the 3D camera (box 24), wherein the mobile X-ray detector has a X-ray receiving portion on a planar surface and a plurality of passive markers provided on the planar surface having the X-ray receiving portion; detecting the plurality of passive markers and the markers' pattern in the acquired digital 3D image (box 25), wherein the pattern of the markers' defines a plane of the mobile X-ray detector having the X-ray receiving portion; estimating the plane of the mobile X-ray detector's X-ray receiving portion (box 26); estimating 6 DOF pose of the mobile X-ray detector (box 27), wherein the 6 DOF pose defines the position of the mobile X-ray detector in the 3D camera's coordinate system; and transforming the position of the mobile X-ray detector in the 3D camera's coordinate system into a position in the X-ray base coordinate system which defines an aligned position (box 28); and automatically positioning the X-ray source to the aligned position by driving the X-ray tube robot system 120 (box 29) which brings the X-ray source in alignment with the mobile X-ray detector.

In some embodiments, using the position of the mobile X-ray detector in the X-ray base coordinate system, an aligned position for the X-ray source is determined. The aligned position for the X-ray source is the position in which the X-ray source is in alignment with the mobile X-ray detector for X-ray examination.

In some embodiments, the 3D camera is an infrared (IR)-based camera with IR depth sensor capability and the image acquired by the 3D camera is an IRD image. As discussed above in connection with the discussion of computing the 6 DOF position of the X-ray detector, where the 3D camera is an IR-based camera, the plurality of passive markers are IR reflective markers.

In other embodiments, the 3D camera is a visible light spectrum-based camera that is configured with a visible light spectrum depth sensor capability and the image acquired by the 3D camera is an RGBD image. In these embodiments, the plurality of passive markers have a contrasting color with respect to the mobile X-ray detector's color so that the markers are distinguishable from the color of the mobile X-ray detector.

In both the IR depth sensing embodiment and the RGB depth sensing embodiment, the passive markers are used for detecting the mobile X-ray detector. In some embodiments, the passive markers comprise radial corner markers 220 and smaller point markers 210. The larger radial corner markers 220 are shaped for marking each of the four corners of the mobile X-ray detector. The smaller point markers 210 are for the identification and validation of the larger radial corner markers such that we know which corner of the detector is observed at the specific image location. In other embodiments, other shapes and configuration and placement of the passive markers can also be used for detector detection.

The X-ray system and methods disclosed herein provides improved X-ray image quality as a result of better alignment between the X-ray source and the mobile X-ray detector. The efficiency of the operation of the X-ray system will be improved by automating the alignment of the X-ray source to the mobile X-ray detector which will mean increased patient throughput. The repeatability of the X-ray examination will also improve because the accuracy of the alignment between the X-ray source and the mobile X-ray detector will no longer depend on the experience level of the X-ray technician. Also, the barrier to integrating this automated alignment feature into the X-ray systems is low because the cost of implementing the automation feature is low.

According to another aspect, a non-transitory computer readable medium storing computer program instructions for determining the position of a mobile X-ray detector in an X-ray system is disclosed. The computer program instructions when executed by a processor cause the processor to perform operations comprising: acquiring a digital 3D image of the mobile X-ray detector using the 3D camera, wherein the mobile X-ray detector has a X-ray receiving portion on a planar surface and a plurality of passive markers provided on the planar surface having the X-ray receiving portion; detecting the plurality of passive markers and the markers' pattern in the digital 3D image, wherein the pattern of the markers' defines the plane of the mobile X-ray detector having the X-ray receiving portion; estimating the plane of the mobile X-ray detector's X-ray receiving portion; estimating 6 DOF pose of the mobile X-ray detector, wherein the 6 DOF pose defines the position of the mobile X-ray detector in the 3D camera's coordinate system; and transforming the position of the mobile X-ray detector in the 3D camera's coordinate system into a position in the X-ray base coordinate system.

According to another aspect, a non-transitory computer readable medium storing computer program instructions for automatically aligning a positionable X-ray source of an X-ray system in alignment with a mobile X-ray detector is disclosed. The computer program instructions when executed by a process causes the processor to perform operations comprising: manually positioning the mobile X-ray detector at a position to examine a region of interest on a patient, wherein the mobile X-ray detector has a X-ray receiving portion on a planar surface and a plurality of passive markers provided on the planar surface having the X-ray receiving portion; positioning the 3D camera so that the mobile X-ray detector is within the field of view of the 3D camera; automatically determining the position of the mobile X-ray detector using the 3D camera, wherein automatically determining the position of the mobile X-ray detector comprises: acquiring a digital 3D image of the mobile X-ray detector using the 3D camera, wherein the mobile X-ray detector has a X-ray receiving portion on a planar surface and a plurality of passive markers provided on the planar surface having the X-ray receiving portion; detecting the plurality of passive markers and the markers' pattern in the acquired digital 3D image, wherein the pattern of the passive markers' defines a plane of the mobile X-ray detector having the X-ray receiving portion; estimating the plane of the mobile X-ray detector's X-ray receiving portion; estimating 6 DOF pose of the mobile X-ray detector, wherein the 6 DOF pose defines the position of the mobile X-ray detector in the 3D camera's coordinate system; and transforming the position of the mobile X-ray detector in the 3D camera's coordinate system into a position in the X-ray base coordinate system which defines an aligned position; and automatically positioning the X-ray source to the aligned position by driving the X-ray tube robot system which brings the X-ray source in alignment with the mobile X-ray detector.

Figure 1B:
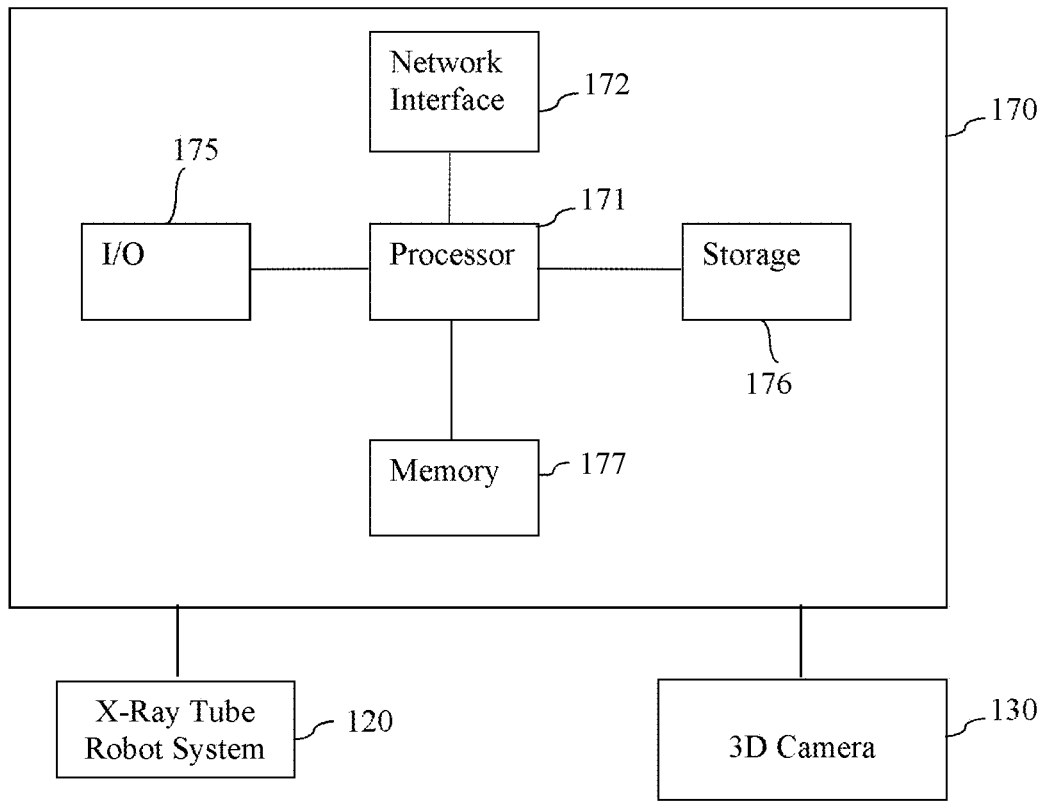
FIG. 1B is a high-level block diagram of the system controller 170 capable of implementing the method of the present disclosure.

Referring to FIG. 1B, the above-described methods can be implemented on the X-ray system 100 using the system controller 170 that is properly equipped with a computer processor 171, which controls the overall operation of the system controller 170 by executing computer program instructions which define such operation. The computer program instructions can be stored in a data storage device 176 (e.g. solid state memory units, magnetic disks, etc.) and loaded into memory 177 when execution of the computer program instructions is desired. Thus, the steps of the methods described above can be computer program instructions stored in the memory 177 and/or data storage device 176 and controlled by the processor 171 executing the computer program instructions. The 3D camera 130 can be connected to the system controller 170 to input the digital 3D image data to the system controller 170. The 3D camera 130 and the system controller 170 can be directly connected or may communicate wirelessly through a network or other wireless communication protocol. The X-ray tube robot system 120 can also be connected to the system controller 170. The X-ray tube robot system 120 and the system controller 170 can be directly connected or may communicate through a network or other wireless communication protocol.

The system controller 170 can communicate with the X-ray tube robot system 120 to control the positioning and orientation of the X-ray source 122 and to control X-ray image acquisition by the mobile X-ray detector 110. X-ray images acquired by the X-ray detector 110 can be input to the system controller 170. The system controller 170 also includes one or more network interfaces 172 for communicating with other devices via a communication network. The system controller 170 also includes other input/output devices 175 that enable user interaction with the system controller 170. Such input/output devices 175 can be touch-screen interface, display, keyboard, mouse, speakers, buttons, etc. One skilled in the art would recognize that an implementation of the system controller 170 can contain other components as well, and that FIG. 1B is a high-level block diagram of some of the components of such a control system for illustrative purposes.

The description of various embodiments is provided to enable any person skilled in the art to practice the disclosure. The various modifications to these embodiments will be readily apparent to those skilled in the art, and the generic principles defined herein may be applied to other embodiments without the use of inventive faculty. The present disclosure is not intended to be limited to the embodiments shown herein, but is to be accorded the widest scope consistent with the principles and novel features disclosed herein.

What is claimed is:

1. A method for determining the position of a mobile X-ray detector in an X-ray system, wherein the X-ray system is provided with a 3D camera, the method comprising:
   acquiring a digital 3D image of the mobile X-ray detector using the 3D camera, wherein the mobile X-ray detector has a X-ray receiving portion on a planar surface and a plurality of passive markers provided on the planar surface having the X-ray receiving portion;
   detecting the plurality of passive markers and the markers' pattern in the digital 3D image, wherein the pattern of the markers' defines the plane of the mobile X-ray detector having the X-ray receiving portion;
   estimating the plane of the mobile X-ray detector's X-ray receiving portion;
   estimating 6 DOF pose of the mobile X-ray detector, wherein the 6 DOF pose defines the position and orientation of the mobile X-ray detector in the 3D camera's coordinate system; and
   transforming the 6DOF pose of the mobile X-ray detector in the 3D camera's coordinate system into the corresponding position and orientation in the X-ray base coordinate system,
   wherein the mobile X-ray detector has four corners and the plurality of passive markers,
   are provided in a specific corner pattern at each of the four corners designating the particular corner,
   wherein detecting the plurality of passive markers and the marker's pattern in the digital 3D image comprises determining the specific corner patterns, and determining the mobile X-ray detector's orientation.

2. The method of claim 1, wherein determining the mobile X-ray detector's orientation comprises matching the specific corner patterns to a pre-defined detector template.

3. The method of claim 1, wherein the plurality of passive markers comprise radial corner markers and a plurality of point markers.

4. The method of claim 1, wherein the 3D camera is an infrared (IR)-based camera and the plurality of passive markers are IR reflective markers, and the 3D camera is configured and adapted with an IR depth sensing capability.

5. The method of claim 1, wherein the 3D camera is a visible light spectrum-based camera and the plurality of passive markers have a color that is visibly distinguishable from the color of the mobile X-ray detector, and the 3D camera is configured and adapted with a visible light spectrum depth sensing capability.

6. A method for automatically aligning a positionable X-ray source of an X-ray system in alignment with a mobile X-ray detector, wherein the X-ray system is equipped with a 3D camera having a field of view, the method comprising:

manually positioning the mobile X-ray detector at a position to examine a region of interest on a patient, wherein the mobile X-ray detector has a X-ray receiving portion on a planar surface and a plurality of passive markers provided on the planar surface having the X-ray receiving portion;

positioning the 3D camera so that the mobile X-ray detector is within the field of view of the 3D camera;

automatically determining the position of the mobile X-ray detector using the 3D camera, wherein automatically determining the position of the mobile X-ray detector comprises:

acquiring a digital 3D image of the mobile X-ray detector using the 3D camera, wherein the mobile X-ray detector has a X-ray receiving portion on a planar surface and a plurality of passive markers provided on the planar surface having the X-ray receiving portion;

detecting the plurality of passive markers and the markers' pattern in the acquired digital 3D image, wherein the pattern of the passive markers' defines a plane of the mobile X-ray detector having the X-ray receiving portion;

estimating the plane of the mobile X-ray detector's X-ray receiving portion;

estimating 6 DOF pose of the mobile X-ray detector, wherein the 6 DOF pose defines the position of the mobile X-ray detector in the 3D camera's coordinate system; and transforming the 6DOF pose of the mobile X-ray detector in the 3D camera's coordinate system into a position in the X-ray base coordinate system which defines an aligned position; and automatically positioning the X-ray source to the aligned position by driving the X-ray tube robot system which brings the X-ray source in alignment with the mobile X-ray detector, wherein the mobile X-ray detector has four corners and the plurality of passive markers are provided in a specific corner pattern at each of the four corners designating the particular corner, wherein detecting the plurality of passive markers and the marker's pattern in the digital 3D image comprises determining the specific corner patterns, and determining the mobile X-ray detector's orientation.

7. The method of claim 6, wherein determining the mobile X-ray detector's orientation comprises matching the specific corner patterns to a pre-defined detector template.

8. The method of claim 6, wherein the plurality of passive markers comprise radial corner markers and a plurality of point markers.

9. The method of claim 6, wherein the 3D camera is an infrared (IR)-based camera and the plurality of passive markers are IR reflective markers, and the 3D camera is configured and adapted with an IR depth sensing capability.

10. The method of claim 6, wherein the 3D camera is a visible light spectrum-based camera and the plurality of passive markers have a color that is visibly distinguishable from the color of the mobile X-ray detector, and the 3D camera is configured and adapted with a visible light spectrum depth sensing capability.

11. A non-transitory computer readable medium storing computer program instructions for determining the position of a mobile X-ray detector in an X-ray system, wherein the X-ray system is provided with a 3D camera, the computer program instructions when executed by a processor cause the processor to perform operations comprising:

acquiring a digital 3D image of the mobile X-ray detector using the 3D camera, wherein the mobile X-ray detector has a X-ray receiving portion on a planar surface and a plurality of passive markers provided on the planar surface having the X-ray receiving portion;

detecting the plurality of passive markers and the markers' pattern in the digital 3D image, wherein the pattern of the markers' defines the plane of the mobile X-ray detector having the X-ray receiving portion;

estimating the plane of the mobile X-ray detector's X-ray receiving portion;

estimating 6 DOF pose of the mobile X-ray detector, wherein the 6 DOF pose defines the position of the mobile X-ray detector in the 3D camera's coordinate system; and transforming the 6 DOF pose of the mobile X-ray detector in the 3D camera's coordinate system into a position in the X-ray base coordinate system, wherein the mobile X-ray detector has four corners and the plurality of passive markers are provided in a specific corner pattern at each of the four corners designating the particular corner, wherein detecting the plurality of passive markers and the marker's pattern in the digital 3D image comprises determining the specific corner patterns, and determining the mobile X-ray detector's orientation.

12. The non-transitory computer readable medium of claim 11, wherein determining the mobile X-ray detector's orientation comprises matching the specific corner patterns to a pre-defined detector template.

13. The method of claim 11, wherein the plurality of passive markers comprise radial corner markers and a plurality of point markers.

14. The non-transitory computer readable medium of claim 11, wherein the 3D camera is an infrared (IR)-based camera and the plurality of passive markers are IR reflective markers, and the 3D camera is configured and adapted with an IR depth sensing capability.

15. The non-transitory computer readable medium of claim 11, wherein the 3D camera is a visible light spectrum-based camera and the plurality of passive markers have a color that is visually distinguishable from the color of the mobile X-ray detector, and the 3D camera is configured and adapted with a visible light spectrum depth sensing capability.

16. A non-transitory computer readable medium storing computer program instructions for automatically aligning a positionable X-ray source of an X-ray system in alignment with a mobile X-ray detector, wherein the X-ray system is equipped with a 3D camera having a field of view, the method comprising:

manually positioning the mobile X-ray detector at a position to examine a region of interest on a patient, wherein the mobile X-ray detector has a X-ray receiving portion on a planar surface and a plurality of passive markers provided on the planar surface having the X-ray receiving portion;

positioning the 3D camera so that the mobile X-ray detector is within the field of view of the 3D camera;

automatically determining the position of the mobile X-ray detector using the 3D camera, wherein automatically determining the position of the mobile X-ray detector comprises:

acquiring a digital 3D image of the mobile X-ray detector using the 3D camera, wherein the mobile X-ray detector has a X-ray receiving portion on a planar surface and a plurality of passive markers provided on the planar surface having the X-ray receiving portion;

detecting the plurality of passive markers and the markers' pattern in the acquired digital 3D image, wherein the pattern of the passive markers' defines a plane of the mobile X-ray detector having the X-ray receiving portion;

estimating the plane of the mobile X-ray detector's X-ray receiving portion;

estimating 6 DOF pose of the mobile X-ray detector, wherein the 6 DOF pose defines the position of the mobile X-ray detector in the 3D camera's coordinate system; and transforming the 6 DOF pose of the mobile X-ray detector in the 3D camera's coordinate system into a position in the X-ray base coordinate system which defines an aligned position; and automatically positioning the X-ray source to the aligned position by driving the X-ray tube robot system which brings the X-ray source in alignment with the mobile X-ray detector, wherein the mobile X-ray detector has four corners and the plurality of passive markers are provided in a specific corner pattern at each of the four corners designating the particular corner, wherein detecting the plurality of passive markers and the marker's pattern in the digital 3D image comprises determining the specific corner patterns, and determining the mobile X-ray detector's orientation.

17. The non-transitory computer readable medium of claim 16, wherein determining the mobile X-ray detector's orientation comprises matching the specific corner patterns to a pre-defined detector template.

18. The method of claim 16, wherein the plurality of passive markers comprise radial corner markers and a plurality of point markers.

19. The non-transitory computer readable medium of claim 16, wherein the 3D camera is an infrared (IR)-based camera and the plurality of passive markers are IR reflective markers, and the 3D camera is configured and adapted with an IR depth sensing capability.

20. The non-transitory computer readable medium of claim 16, wherein the 3D camera is a visible light spectrum-based camera and the plurality of passive markers have a color that is visibly distinguishable from the color of the mobile X-ray detector, and the 3D camera is configured and adapted with a visible light spectrum depth sensing capability.

* * * * *